United States Patent
Knoedler

(10) Patent No.: US 12,193,963 B2
(45) Date of Patent: Jan. 14, 2025

(54) MONITOR DEVICE FOR AN OSTOMY APPLIANCE

(71) Applicant: Coloplast A/S, Humlebaek (DK)

(72) Inventor: Stephanie Knoedler, Nivaa (DK)

(73) Assignee: Coloplast A/S, Humlebaek (DK)

( * ) Notice: Subject to any disclaimer, the term of this patent is extended or adjusted under 35 U.S.C. 154(b) by 664 days.

(21) Appl. No.: 17/432,495

(22) PCT Filed: Feb. 20, 2020

(86) PCT No.: PCT/DK2020/050045
§ 371 (c)(1),
(2) Date: Aug. 20, 2021

(87) PCT Pub. No.: WO2020/169162
PCT Pub. Date: Aug. 27, 2020

(65) Prior Publication Data
US 2022/0241104 A1 Aug. 4, 2022

(30) Foreign Application Priority Data
Feb. 21, 2019 (DK) .......................... PA 2019 70111

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC .............................. A61F 5/4404; A61F 5/443
See application file for complete search history.

(56) References Cited

U.S. PATENT DOCUMENTS

| | | | |
|---|---|---|---|
| 6,171,289 B1 | 1/2001 | Millot et al. | |
| 8,821,465 B2 * | 9/2014 | Hanuka | A61F 5/4407 604/333 |
| 2008/0156092 A1 * | 7/2008 | Boiarski | A61F 5/4404 73/304 R |
| 2017/0140103 A1 | 5/2017 | Angelides | |
| 2017/0360592 A1 * | 12/2017 | Carrubba | A61F 5/445 |
| 2018/0228945 A1 * | 8/2018 | Guirguis | A61M 1/66 |
| 2019/0133812 A1 * | 5/2019 | Seres | A61F 5/4404 |
| 2021/0386368 A1 * | 12/2021 | Carlsson | C08L 33/10 |

FOREIGN PATENT DOCUMENTS

WO 2007098762 A1 9/2007

* cited by examiner

*Primary Examiner* — Mohamed Barakat
(74) *Attorney, Agent, or Firm* — Coloplast Corp., Coloplast A/S; Nick Baumann

(57) ABSTRACT

Disclosed is a monitor device (6) for coupling to a sensor assembly of an ostomy appliance, the monitor device comprising: a monitor device housing (100), electronic circuitry, and an appliance interface (424) configured for coupling the monitor device to the sensor assembly, the appliance interface comprises a plurality of terminals (212) for connecting with a plurality of electrodes of the sensor assembly, wherein a coupling element of the sensor assembly is receivable by the appliance interface through an interface opening. The monitor device comprises a transparent part located near the interface opening.

20 Claims, 8 Drawing Sheets

MONITOR DEVICE FOR AN OSTOMY APPLIANCE

The present disclosure relates to monitor device for attachment to a base plate for an ostomy appliance. In particular the present disclosure relates to a monitor device for electronically monitoring properties of an ostomy appliance or components thereof.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY

It is an object of the present disclosure to provide a monitor device to be connected to a sensor assembly for a base plate for facilitating reliable and/or improved detection of risk of failure of an ostomy appliance and/or improved detection of risk of leakage. The disclosed monitor device may be provided to facilitate detection of risk of failure and/or risk of leakage with respect to an adhesive base plate of the ostomy appliance.

Furthermore, it is an object of the present disclosure to provide a monitor device, which is easy and intuitive to use, and which facilitates use and maintenance of the device in accordance with its intended purpose.

Thus, the present disclosure relates to a monitor device for an ostomy appliance, such as a monitor device for coupling to a sensor assembly of an ostomy appliance. The monitor device comprises: a monitor device housing, an electronic circuitry, and an appliance interface configured for coupling the monitor device to the sensor assembly. The appliance interface comprises a plurality of terminals for connecting with a plurality of electrodes of the sensor assembly. A coupling element of the sensor assembly is receivable by the appliance interface through an interface opening. The monitor device comprises a transparent part, and wherein the transparent part is located near the interface opening.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
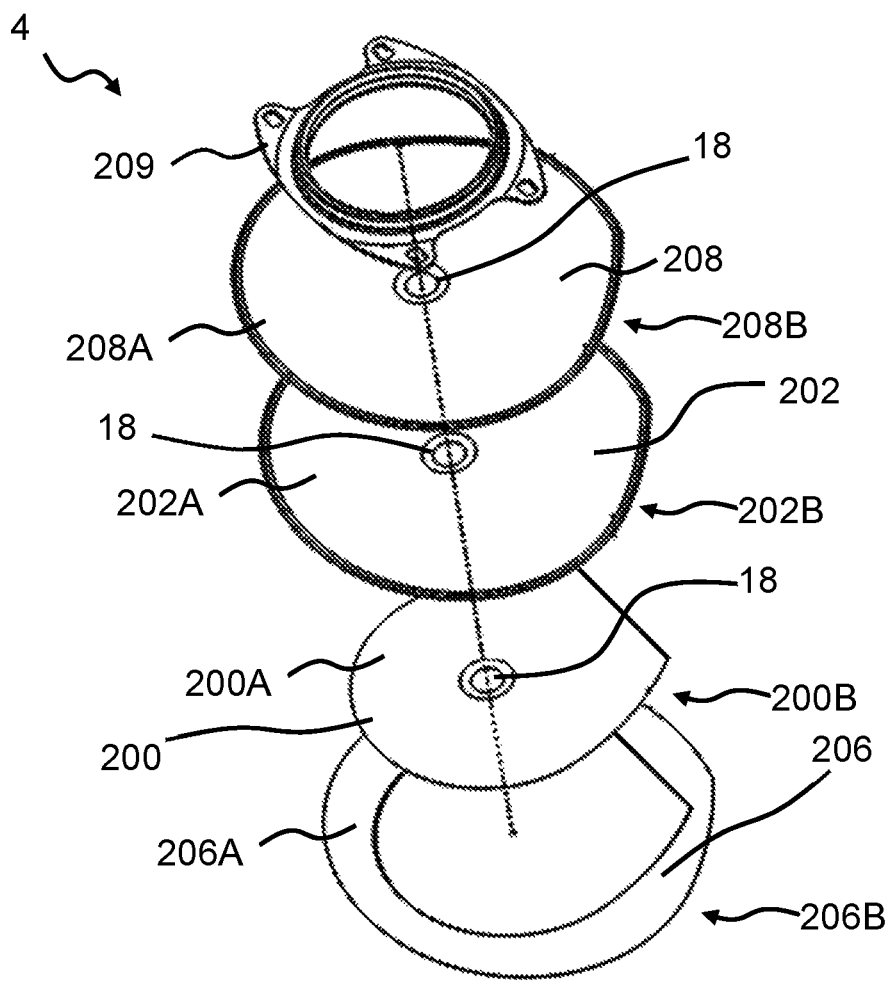
FIG. 1 schematically illustrates an exploded view of an exemplary base plate.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Disclosed is a monitor device for coupling to a sensor assembly of an ostomy appliance, such as for attachment of a base plate or a separate sensor patch to be applied to the base plate.

The ostomy appliance comprises a base plate and an ostomy pouch (also referred to as an ostomy bag). The ostomy appliance may be a colostomy appliance, an ileostomy appliance, or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The proximal surface of the first adhesive layer may be configured to adhere to the user's skin. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface. The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g. such that the proximal surface of the second adhesive layer forms an adhesive rim surrounding the first adhesive layer.

Different ratio of contents may change properties of the first adhesive layer and/or the second adhesive layer. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second adhesive layer may form part of the adhesive surface of the base plate adapted for attachment of the base plate to the skin surface of the user. The first adhesive layer and the second adhesive layer may form the adhesive surface of the base plate adapted for attachment of the base plate to the skin surface of the user.

The first adhesive layer and/or the second adhesive layer may surround an opening, such as a stomal opening. For example, the first adhesive layer may have a stomal opening, such as a first adhesive stomal opening. The second adhesive layer may have a stomal opening, such as a second adhesive stomal opening.

The base plate may comprise a release liner, which may be peeled off by the user prior to applying the base plate to the skin. The release liner may be configured to protect the adhesive layers prior to applying the base plate to the skin. The release liner may comprise a distal surface and a proximal surface. The release liner may be configured to, e.g. prior to applying the base plate to the skin, covering the proximal surface of the first adhesive layer and/or covering the proximal surface of the second adhesive layer, such as the proximal surface of the second adhesive layer not covered by the first adhesive layer. The distal surface of the release liner may be configured to, e.g. prior to applying the base plate to the skin, face the proximal surface of the first adhesive layer and/or the proximal surface of the second adhesive layer, such as the proximal surface of the second adhesive layer not covered by the first adhesive layer.

The base plate may comprise a backing layer. The backing layer may be a protective layer protecting the adhesive layers, such as the first adhesive layer and/or the second adhesive layer from external strains and stress during use. Furthermore, the backing layer may also cover the adhesive layers, such as the first adhesive layer and/or the second adhesive layer, such that the adhesive layers do not adhere to clothes worn on top of the base plate. The backing layer may comprise a distal surface and a proximal surface. The distal surface of the backing layer may be configured to face away from the skin of the user. The proximal surface of the backing layer may be facing the second adhesive layer. The second adhesive layer may be provided on the proximal surface of the backing layer. The backing layer may have a stomal opening, such as a backing layer stomal opening.

The base plate may comprise a stomal opening. Some or each of the layers of the base plate may comprise stomal openings for collectively forming a stomal opening of the base plate. The stomal opening may be provided in a centre portion of the base plate. The centre portion of the base plate may be surrounding the stomal opening. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from the proximal side of the base plate to a distal side of the base plate. The size and/or shape of the stomal opening may typically be adjusted by the user or nurse before application of the base plate to accommodate the user's stoma. The stomal opening(s) may have a centre point.

A sensor patch may be provided for attachment to a base plate for an ostomy appliance, such as the base plate as described above. Such as to facilitate detection of moisture propagation in the adhesive material provided for attaching the base plate to the skin surface of a user as well as detection of increased risk of leakage. For example, the sensor patch may allow electronic measurements of performance of the base plate and/or to facilitate detection of increasing risks of leakage and/or to facilitate detection of decreasing adherence of the base plate to the skin of the user.

The sensor patch may be adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of the first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly may comprise a plurality of electrodes. The plurality of electrodes may include a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g. when seen in the axial direction.

The sensor patch may comprise a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, may form the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The first adhesive sensor layer may surround an opening, such as the stomal opening and/or an opening larger than the stomal opening.

The sensor patch may comprise a second adhesive sensor layer, e.g. with a proximal side and a distal side. The second adhesive sensor layer may be arranged on a distal side of the sensor assembly. The distal side of the second adhesive sensor layer may be configured to adhere to the proximal surface of the base plate, such as the proximal surface of the first adhesive layer of the base plate. The second adhesive sensor layer may be made of a second adhesive sensor material, such as the first composition, the second composition, the third composition, or a fourth composition. The fourth composition may comprise one or more polyisobutenes and/or styrene-isoprene-styrene. The fourth composition may comprise one or more hydrocolloids. The fourth composition may comprise one or more water soluble or water swellable hydrocolloids. The fourth composition may be a pressure sensitive adhesive composition suitable for medical purposes comprising a rubbery elastomeric base and one or more water soluble or water swellable hydrocolloids. The second adhesive sensor material may be the same as the first adhesive sensor material.

The second adhesive sensor layer may surround an opening, such as the stomal opening and/or an opening larger than the stomal opening.

The sensor assembly comprising the plurality of electrodes may be arranged on the distal side of the first adhesive sensor layer and/or on the proximal side of the second adhesive sensor layer. The plurality of electrodes of the sensor assembly may be arranged in relation to the inner and/or outer rim portions of the first adhesive sensor layer and/or second adhesive sensor layer. In particular, the plurality of electrodes may be arranged such as to measure over parts of the adhesive layers where the adhesive layers have a substantially uniform thickness. Such arrangement may facilitate reliability of the measurements and/or the subsequent interpretation of the measured values. The plurality of electrodes of the sensor assembly may form loops, such as open loops or closed loops, e.g. surrounding the stomal opening(s), e.g. surrounding the centre point. The first electrode may form a first loop, the second electrode may form a second loop, the third electrode may form a third loop, the fourth electrode may form a fourth loop, the fifth electrode may form a fifth loop, and/or the sixth electrode may form a sixth loop. An electrode, such as the first electrode, may form a plurality of loops, e.g. the first electrode may form a plurality of first loops, e.g. including a first primary loop, a first secondary loop, a first tertiary loop, etc.

A radial distance from the centre point to the second loop may be less than the radial distance from the centre point to the first loop. A radial distance from the centre point to the third loop may be less than the radial distance from the centre point to the second loop. A radial distance from the centre point to the fourth loop may be less than the radial distance from the centre point to the third loop. A radial distance from the centre point to the fifth loop may be less than the radial distance from the centre point to the fourth loop. A radial distance from the centre point to the sixth loop may be less than the radial distance from the centre point to the fifth loop.

The sensor patch may comprise one or more sensor release liner(s), such as a first sensor release liner and/or a second sensor release liner.

The first sensor release liner may comprise a distal surface and a proximal surface. The first sensor release liner may be arranged to protect the first adhesive sensor layer, e.g. the distal surface of the first sensor release liner may face the proximal surface of the first adhesive sensor layer. The first sensor release liner may be configured to be peeled off by the user prior to application of the base plate with the attached sensor patch to the skin. The layer of the first adhesive sensor material may be laid out on the distal side of the first sensor release liner.

The second sensor release liner may comprise a distal surface and a proximal surface. The second sensor release liner may be arranged to protect the second adhesive sensor layer, e.g. the proximal surface of the second sensor release liner may face the distal surface of the second adhesive sensor layer. The second sensor release liner may be configured to be peeled off by the user prior to attaching the sensor patch to the base plate. The layer of the second adhesive sensor material may be laid out on the proximal side of the second sensor release liner.

The sensor assembly may comprise a monitor interface. The monitor interface may be configured for electrically and/or mechanically connecting the sensor assembly, such as the plurality of electrodes of the sensor assembly, to the monitor device. The monitor interface may be configured for wirelessly connecting the sensor assembly, such as the electrodes of the sensor assembly, to the monitor device. The monitor interface may be configured to electrically and/or mechanically couple the monitor device to the sensor assembly.

The monitor interface may comprise, e.g. as part of a first connector of the monitor interface, a coupling element for forming a mechanical connection, such as a releasable coupling between the monitor device and the sensor assembly. The coupling element may be configured to engage with an appliance interface of the monitor device for releasably coupling the monitor device to the sensor assembly.

The monitor interface may comprise, e.g. as part of a first connector of the monitor interface, a plurality of terminals, such as two, three, four, five, six, seven or more terminals, for forming electrical connections with respective terminals of the monitor device. The plurality of terminals may be provided on the coupling element. The plurality of terminals may be connected to the plurality of electrodes of the sensor assembly, e.g. each of the plurality of terminals may be connected to a respective electrode of the plurality of electrodes of the sensor assembly. Alternatively or additionally, the plurality of electrodes may form the plurality of terminals, e.g. each of the plurality of electrodes may form a respective terminal of the plurality of terminals of the monitor interface.

The coupling element may be configured to engage with the monitor device by a linear motion in an engagement direction of the monitor device relative to the sensor assembly. The coupling element may be configured to disengage with the monitor device by a linear motion in a disengagement direction of the monitor device relative to the sensor assembly. The coupling element may be substantially flat. The coupling element may comprise a first surface and a second surface. The second surface may be opposite the first surface. The second surface may be configured to be facing towards the skin of the user. The first surface may be configured to be facing away from the skin of the user.

The disclosed sensor patch could be combined with the base plate, such as to form a monolithic, one-piece base plate, e.g. integrated with a sensor assembly part, such as the sensor assembly part as described above. For example, the base plate may comprise a sensor assembly, such as the sensor assembly as described with respect to the sensor patch. For example, the sensor assembly may be positioned between the first adhesive layer and the second adhesive layer. The distal surface of the first adhesive layer may be facing the proximal side of the sensor assembly and/or the distal side of the sensor assembly may be facing the proximal side of the second adhesive layer. For example, the first adhesive layer and/or the second adhesive layer of the base plate may be provided as described with respect to the first adhesive sensor layer and/or the second adhesive sensor layer, respectively.

The disclosed monitor device is configured to be connected to the sensor assembly to facilitate collection and/or evaluation of sensor data retrieved from the plurality of electrodes of the sensor assembly. The monitor device may be configured to retrieve sensor data from the plurality of electrodes of the sensor assembly. The monitor device may be configured to store, process and/or transmit sensor data retrieved from the plurality of electrodes of the sensor assembly.

The monitor device may comprise a monitor device housing. The monitor device housing may be made of a plastic material, such as a thermoplastic material. The monitor device, such as the monitor device housing, may be elongated having a first end and a second end. The monitor device, such as the monitor device housing, may have a length or maximum extension along a longitudinal axis in the range from 10 mm to 150 mm. The monitor device, such as the monitor device housing, may have a width or maximum extension perpendicular to the longitudinal axis in the range from 5 mm to 30 mm. The monitor device, such as the monitor device housing, may be curve-shaped.

The monitor device may comprise electronic circuitry, e.g. electronic circuitry for receiving, processing, storing and/or transmitting signals and/or data. The electronic circuitry may, for example, include a processor, a wireless communication unit, memory etc. The electronic circuitry may be enclosed by the monitor device housing.

The monitor device may comprise an appliance interface, such as an appliance interface configured for coupling the monitor device to the sensor assembly of the base plate and/or sensor patch, such as for electrically and/or mechanically coupling the monitor device to the sensor assembly. The appliance interface may comprise a plurality of terminals, such as two, three, four, five, six, seven or more terminals, for connecting with a plurality of electrodes of the sensor assembly. The plurality of terminals of the appliance interface may be configured for connecting with terminals of the sensor assembly, such as respective terminals of the sensor assembly.

The coupling element of the sensor assembly, as described above, may be receivable by the appliance interface through an interface opening. The monitor device may have a first major side and a second major side opposite the first major side. The first major side may be configured to face away from the user when the monitor device is coupled to the sensor assembly and the ostomy appliance is placed on the skin of the user. The interface opening may be provided in a first rim part between the first major side and the second major side. The first rim part may be substantially parallel to the length and/or longitudinal axis of the monitor device.

As also described above, the coupling element of the sensor assembly may be configured to be received through the interface opening along an engagement direction. The engagement direction and/or the disengagement direction may be substantially perpendicular to the first rim part. For example, the engagement direction and/or the disengagement direction may be substantially perpendicular to the length and/or longitudinal axis of the monitor device.

The appliance interface may, e.g. additionally, be configured for coupling of the monitor device to a docking station of the ostomy system, e.g. for charging the monitor device and/or for data transfer between the monitor device and the docking station.

The monitor device may comprise a transparent part. The transparent part may, at least partly, allow transmittance of visible light or at least some visible light. Visible light may be light having wavelengths between 380-740 nm. The transparent part may, at least partly, allow transmittance of at least a subset of wavelengths of visible light, such as wavelengths between 565-740 nm, such as between 600-740 nm, such as between 650-740 nm. The transparent part may allow transmission of more than 20%, such as more than 30%, such as more than 40%, such as more than 50%, such as more than 60%, such as more than 70%, such as more than 80% of at least a subset of wavelengths of visible light, such as wavelengths between 565-740 nm, such as between 600-740 nm, such as between 650-740 nm.

Providing the monitor device with a transparent part provides a visual effect of the monitor device as a whole appearing to be smaller, and therefore more appealing in a field where discretion is of a main concern.

The transparent part may allow transmission of less than 100%, such as less than 90%, such as less than 80% of at least a subset of wavelengths of visible light, such as wavelengths between 565-740 nm, such as between 600-740 nm, such as between 650-740 nm. The transparent part may allow transmission of between 20%-95%, such as between 40%-90%, such as between 60%-80%, of at least a subset of wavelengths of visible light, such as wavelengths between 565-740 nm, such as between 600-740 nm, such as between 650-740 nm. For example, the transparent part may be light frosted. For example, the transparent part may be provided in a mould having tiny imperfect surfaces to provide the transparent part with a light frosted surface. Alternatively or additionally, the transparent part may be made of polymers being less than 100% amorphous, e.g. less than 90% amorphous, e.g. less than 80% amorphous. The transparent part may be made of a plastic material, such as acrylic or polycarbonate.

By providing a transparent part that is partly transparent, the transparent part allows for the transmission of light, while at the same time better blending in with the rest of the monitor device. In other words, a transparent part having a transmission of less than 100% may provide for a frosted part, which may provide visual access to the appliance interface without standing out from the monitor device as such.

A surface texture of the transparent part may be similar to a surface texture of the non-transparent parts of the monitor device. Thereby, the appearance despite the transparency of the transparent part may be consistent and/or the tactile feedback to the user may remain unchanged throughout the monitor device as a whole.

The transparent part may be located near the interface opening. For example, the transparent part may be located less than 3 mm, such as less than 2 mm, such as less than 1 mm, such as less than 0.5 mm, from the interface opening. Alternatively or additionally, the transparent part may be located at the interface opening. For example, the transparent part may be forming at least a part of the perimeter of the interface opening.

Providing the transparent part near or at the interface opening provides a visible hint to the user on where to insert the coupling element of the sensor assembly in order to connect the two as intended. The transparent property of the transparent part furthermore provides the visual effect of the interface opening almost appearing bigger and it is easier for the user to see where and how to couple the coupling element and the monitor device.

Furthermore, the provision of the transparent part near or at the interface opening may facilitate visibility of possible dirt accumulated inside the appliance interface. Thereby, the user may be able to see when it is time to clean the monitor device and in particular the appliance interface of the monitor device.

The transparent part may be a window, such as a window providing visual access to part of the interior of the monitor device. The transparent part may be positioned such that the plurality of terminals of the appliance interface is visible through the transparent part. The transparent part may be provided on the first major side, such as the side of the monitor device configured to be facing away from the skin of the user, when the ostomy appliance is applied.

By allowing the user to see the terminals of the appliance interface, the user is provided with the ability to realise if a faulty connection between the monitor device and the sensor assembly may be caused by dirt accumulated in the appliance interface, and the user is able to directly see if it is time to clean the appliance interface to get a proper connection.

Furthermore, providing the transparent part such that the user is able to see the terminals of the appliance interface provides the user with a better understanding of how the device is working, and thereby also enhances the likelihood that the user will be able to insert the coupling element of the sensor assembly as intended into the appliance interface. At the same time the transparent part may provide a cover for the appliance interface, as opposed to leaving the appliance interface completely open. The transparent part may aid in guiding the coupling element to the correct position when inserted through the interface opening.

The transparent part may have an outline similar to the outline of the coupling element of the sensor assembly. A similar outline of the transparent part and the coupling element may further signal to the users where to insert the coupling element.

The transparent part may extend a first distance, e.g. from the interface opening, in a direction substantially perpendicular to the first rim part, e.g. perpendicular to the length and/or longitudinal axis of the monitor device. The first distance may be more than 10%, such as more than 20%, such as more than 35%, such as more than 50%, of a total distance between the first rim part and an opposite second rim part between the first major side and the second major side. For example, the first distance may be more than 10%, such as more than 20%, such as more than 35%, such as more than 50%, of the width of the monitor device. For example, the first distance may be more than 5 mm, such as more than 10 mm.

The transparent part may extend a second distance in a direction substantially parallel to the first rim part, e.g. parallel to the length and/or longitudinal axis of the monitor device. The second distance may be substantially the same as the extension of the interface opening in the direction substantially parallel to the first rim part, e.g. parallel to the length and/or longitudinal axis of the monitor device. For example, the second distance may be between 80-100%, such as between 90-100%, of the extension of the interface opening in the direction substantially parallel to the first rim part, e.g. parallel to the length and/or longitudinal axis of the monitor device.

The monitor device may comprise a locking mechanism configured to lock the coupling element of the sensor assembly in a received position of the appliance interface. For example, the locking mechanism may comprise a locking component, such as a pin configured to engage a hole of the coupling element. The locking component may be positioned on an inside of the interface opening.

The monitor device may comprise a locking element configured to lock and/or unlock the locking mechanism upon user interaction with the locking element. The locking element may form part of the locking mechanism. The locking element may comprise a button and/or a latch for user interaction. The locking element may be engaged to lock the locking mechanism, and/or the locking element may be engaged to unlock the locking mechanism. User interaction with the locking element may comprise deflection of a button, repositioning of a latch, sliding of a slider etc.

The locking element may be configured to rotate relative to the monitor device housing, e.g. about a locking element axis. The locking element axis may be substantially parallel to the first rim part and/or may be substantially parallel to the length and/or longitudinal axis of the monitor device.

The locking element may be configured to provide a haptic and/or acoustic feedback upon engagement to lock and/or unlock the locking mechanism. For example, the locking element may make a "click" sound, which makes the user aware that the device has been locked/unlocked without the necessity of looking at it.

The locking element may comprise the transparent part. For example, the transparent part may be moved together with the locking element when repositioning the locking element to lock and/or unlock the locking mechanism.

The locking element may form the interface opening. For example, the locking element may comprise the interface opening.

The transparent part may have a first colour, e.g. the transparent part may be dyed with a colour. The monitor device housing may have a second colour. The second colour may be different from the first colour. For example, a colour distance between the first colour and the second colour may be more than 10, such as more than 20, e.g. according to CIEDE2000 colour distance metric.

Providing the transparent part and the monitor device housing in different colours may further enhance the user's awareness to the transparent part and thereby to the part of the monitor device to operate in order to couple it to the sensor assembly. This may also be of additional advantage if the transparent part is provided together with the locking element, thereby attention is drawn both to the interface opening and also to the locking element.

For example, the first colour may be a turquoise colour, such as an RGB colour where the green and blue channels are within 20 points (on a colour range of 0-255) of each other, and wherein the red channel is less than the green and blue channels, such as RGB=64, 224, 208, or RGB=178, 255, 255, or RGB=175, 238, 238, or RGB=0, 255, 239, or RGB=72, 209, 204 or 0, 206, 209.

For example, the second colour may be a grey colour, such as an RGB colour wherein the red, green and blue channels are substantially the same, e.g. within 20 points of each other (on a colour range of 0-255).

The monitor device housing may have a primary second colour and/or a secondary second colour. For example, the first major side of the monitor device may be the primary second colour and the second major side of the monitor device may be the secondary second colour. The secondary second colour may be darker than the primary second colour. For example, the secondary second colour may have RGB values that are more than 5, such as more than 10, such as more than 20 points (on a colour range of 0-255) lower than primary second colour. Providing the second major side with a darker colour than the first major side may provide that the monitor device is appearing to be slimmer and thereby more likely to be used. It furthermore indicates to the user which side is to be positioned against the skin.

FIG. 1 schematically illustrates an exploded view of an exemplary base plate 4 of an ostomy appliance. The base plate 4 comprises a first adhesive layer 200 having a distal surface 200A and a proximal surface 200B. During use, the proximal surface 200B of the first adhesive layer 200 adheres to the user's skin. The base plate 4 comprises a second adhesive layer 202 having a distal surface 202A and a proximal surface 202B. As illustrated, the second adhesive layer 202 spans a larger surface area than the first adhesive layer 200, such as to provide a rim of the proximal surface 202 of the second adhesive layer 202 surrounding the proximal surface 200 of the first adhesive layer 200.

The base plate 4 comprises a release liner 206, which may be peeled off by the user prior to applying the base plate 4 to the skin. The release liner 206 comprises a distal surface 206A and a proximal surface 206B. The distal surface 206A of the release liner 206 is covering the proximal surface of the first adhesive layer 200 and covering the proximal surface of the second adhesive layer 202 not covered by the first adhesive layer 200.

The base plate 4 comprises a backing layer 208. The backing layer 208 is a protective layer protecting the adhesive layers, such as the first adhesive layer 200 and/or the second adhesive layer 202 from external strains and stress during use. Furthermore, the backing layer 208 also covers the adhesive layers, such as the first adhesive layer 200 and/or the second adhesive layer 202, such that the adhesive layers 200, 202 does not adhere to clothes worn on top of the base plate 4. The backing layer 208 comprises a distal surface 208A and a proximal surface 208B. The distal surface 208A of the backing layer 208 is configured to face away from the skin of the user. The proximal surface 208B of the backing layer 208 is covering the second adhesive layer 202.

The base plate 4 is a two-part ostomy appliance, thus comprising a coupling ring 209 for coupling an ostomy pouch to the base plate 4, such as to a distal side of the base plate 4.

The base plate 4 comprises a stomal opening. The layers of the base plate 4, such as the first adhesive layer 200, the second adhesive layer 202 and the backing layer 208 as illustrated, may comprise stomal openings 18 for collectively forming the stomal opening of the base plate.

Figure 2:
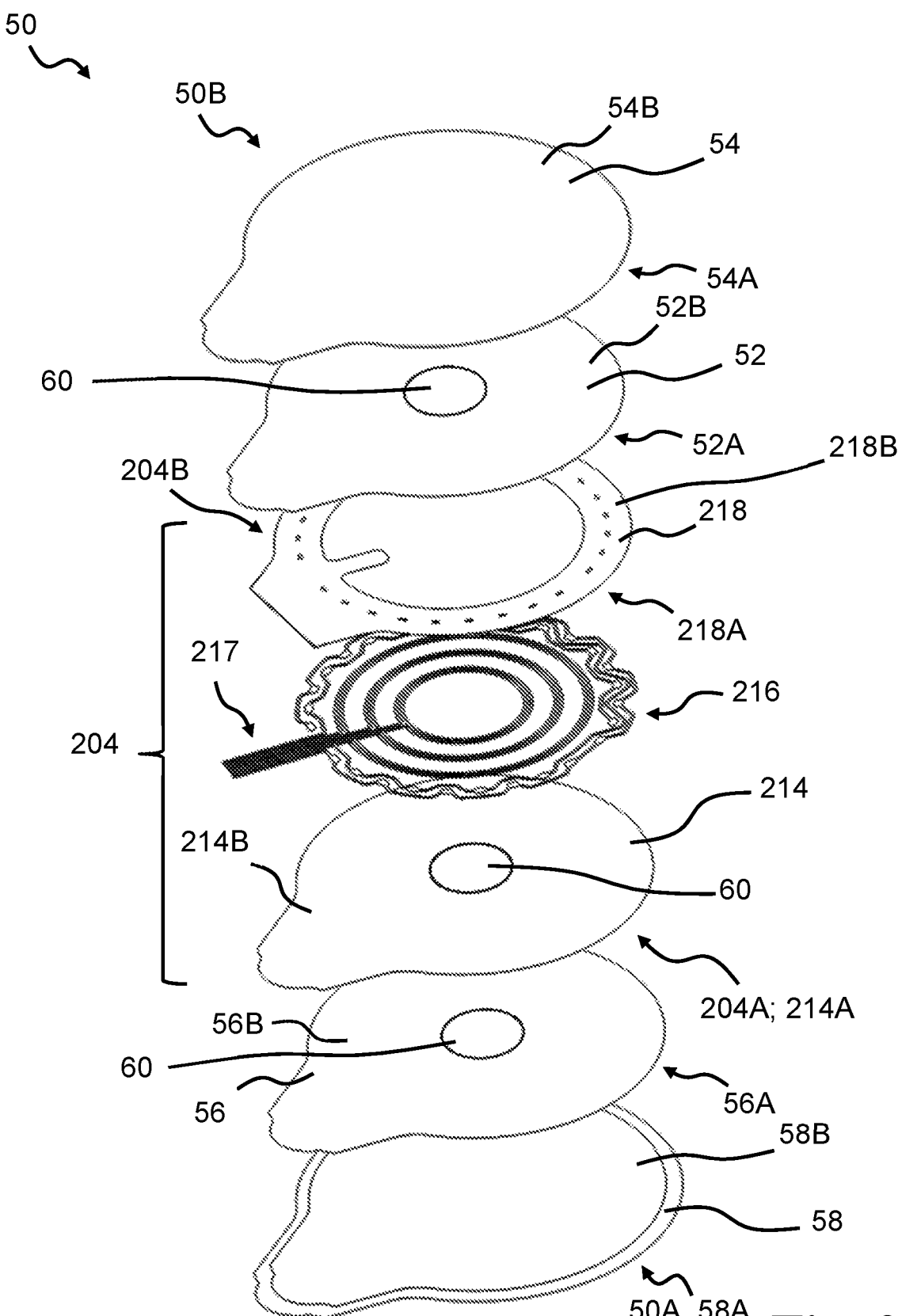
FIG. 2 schematically illustrates an exploded view of an exemplary sensor patch.

FIG. 2 schematically illustrates an exploded view of an exemplary sensor patch 50, such as a sensor patch 50 being adapted for attachment to a base plate, such as the base plate 4 as illustrated in FIG. 1. The sensor patch 50 is configured to be positioned between the skin of the user and the proximal side of the base plate 4. For example, the sensor patch may be adapted for attachment to the first adhesive layer 200, such as the proximal surface 200B of the first adhesive layer 200, of the base plate 4. The sensor patch 50 is configured to be attached to the base plate such that the distal side 50A of the sensor patch 50 is attached to the proximal side of the base plate, such as to the proximal surface 200B of the first adhesive layer 200 of the base plate 4.

The sensor patch 50 comprises a sensor assembly 204 comprising a plurality of electrodes 216. Each electrode 216 has respective connection parts 217 for connecting the plurality of electrodes 216 to respective terminal elements of a monitor device. The sensor assembly 204 may form a sensor assembly layer.

The sensor assembly 204 has a distal side 204A and a proximal side 204B. The sensor assembly 204 comprises a support layer 214 with a proximal surface 214B. The electrodes 216 may be provided, such as formed, on the proximal surface 214B of the support layer 214, e.g. the electrodes 216 may be positioned on the proximal surface 214B of the support layer 214.

The electrode assembly 204 comprises a masking element 218 having a distal surface 218A and a proximal surface 218B. The masking element 218 is configured to electrically insulate at least parts of electrodes 216 from adjacent layers, such as the first adhesive sensor layer 52. The masking element 218 covers or overlap with parts of the electrodes 216 when seen in the axial direction.

The sensor patch 50 comprises a first adhesive sensor layer 52, with a proximal side 52B and a distal side 52A. The first adhesive sensor layer 52 is arranged on the proximal side 204B of the sensor assembly 204. The proximal side 52B of the first adhesive sensor layer 52 is configured to adhere to the user's skin. Thus, after being applied to the base plate, the combined base plate and sensor patch 50 forms an adhesive proximal surface configured to be applied to the skin surface of the user.

The sensor patch comprises a first sensor release liner 54. The first sensor release liner 54 may comprise a distal surface 54A and a proximal surface 54B. The first sensor release liner 54 may be arranged to protect the first adhesive sensor layer 52. The distal surface 54A of the first sensor release liner 54 is facing the proximal surface 52B of the first adhesive sensor layer 52. The first sensor release liner 54 is configured to be peeled off by the user prior to application of the base plate with the attached sensor patch to the skin. The first adhesive sensor layer 52 may be laid out on the distal side 54A of the first sensor release liner 54.

The sensor patch 50 comprises a second adhesive sensor layer 56, with a proximal side 56B and a distal side 56A. The second adhesive sensor layer 56 is arranged on the distal side 204A of the sensor assembly 204. The proximal side 56B of the second adhesive sensor layer 52 is configured to adhere to the base plate, such as the proximal surface of the first adhesive layer of the base plate.

The sensor patch comprises a second sensor release liner 58. The second sensor release liner 58 may comprise a distal surface 58A and a proximal surface 58B. The second sensor release liner 58 may be arranged to protect the second adhesive sensor layer 56. The proximal surface 58B of the second sensor release liner 58 is facing the distal surface 56A of the second adhesive sensor layer 56. The second sensor release liner 58 is configured to be peeled off by the user prior to application of the sensor patch to the base plate. The second adhesive sensor layer 56 may be laid out on the proximal side 58B of the second sensor release liner 58.

The sensor patch 50 comprises a stomal opening. The layers of the sensor patch 50, such as the first adhesive sensor layer 52, the support layer 214 and the second adhesive sensor layer 56, as illustrated, may comprise stomal openings 60 for collectively forming the stomal opening of the sensor patch 50. The stomal opening of the sensor patch is configured to be aligned with the stomal opening of the base plate, such as to collectively form the stomal opening of the combined base plate and sensor patch 50.

Figure 3:
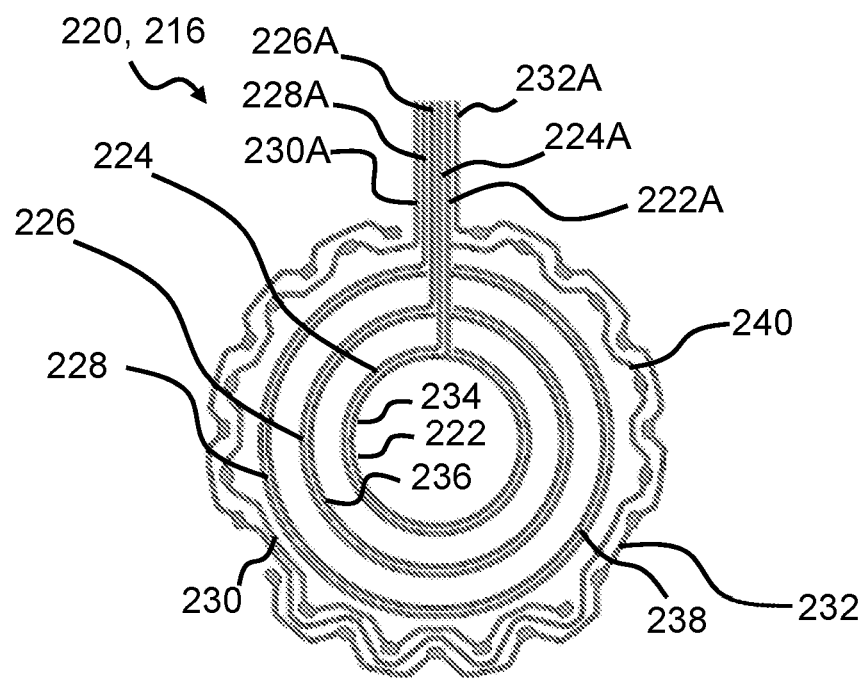
FIG. 3 schematically illustrates an exemplary electrode configuration.

FIG. 3 schematically illustrates an exemplary electrode configuration 220 of electrodes 216 of an exemplary sensor assembly, such as the sensor assembly 204 as described with respect to FIG. 2. The plurality of electrodes 216 comprises a first electrode 222, a second electrode 224, a third electrode 226, a fourth electrode 228, a fifth electrode 230, and a sixth electrode 232.

The first electrode 222 comprises a first connection part 222A and the second electrode 224 comprises a second connection part 224A. The third electrode 226 comprises a third connection part 226A. The fourth electrode 228 comprises a fourth connection part 228A. The fifth electrode 230 comprises a fifth connection part 230A. The sixth electrode 232 comprise a sixth connection part 232A.

The first electrode 222 may be a common ground electrode, such as to form sensors with respect to the remaining electrodes. The first electrode 222 comprises a first electrode part 234 for forming a ground for the second electrode 224. The first electrode 222 comprises a second electrode part 236 for forming a ground for the third electrode 226. The first electrode 222 comprises a third electrode part 238 for forming a ground for the fourth electrode 228. The first electrode 222 comprises a fourth electrode part 240 for forming a ground for the fifth electrode 230 and the sixth electrode 232.

Figure 4:
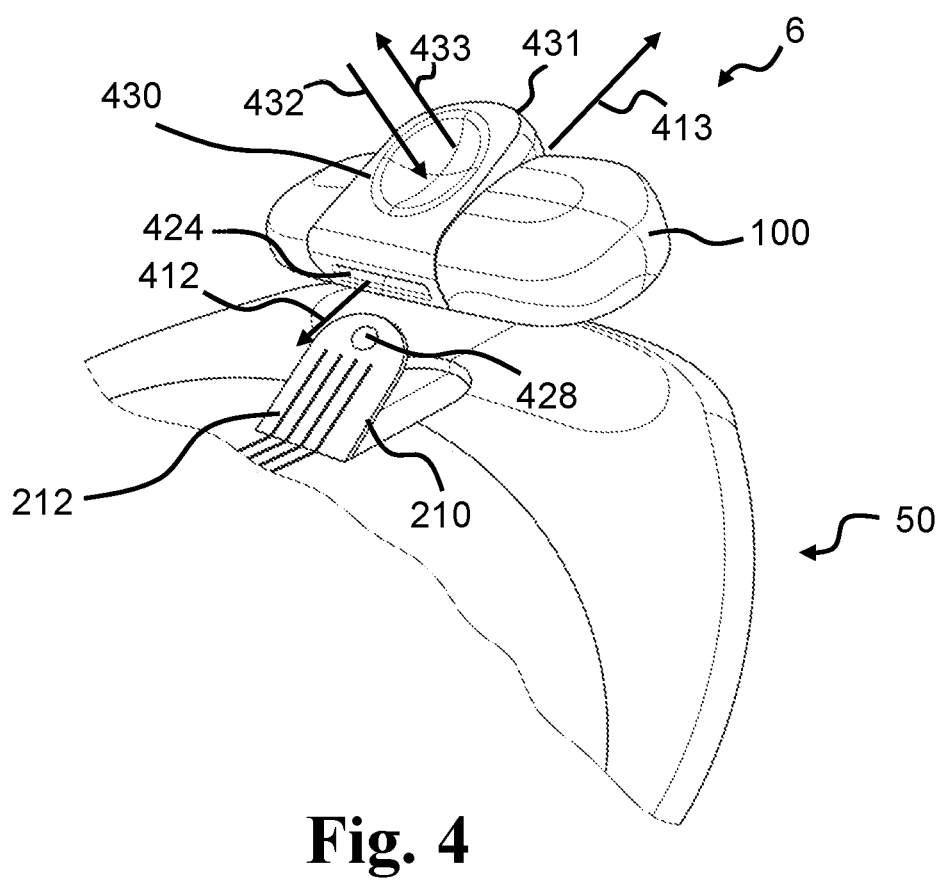
FIG. 4 schematically illustrates part of an exemplary sensor patch.

FIG. 4 schematically illustrates part of an exemplary sensor patch 50, such as the sensor patch 50 as illustrated in FIG. 2, and a monitor device 6. The sensor patch 50 comprises a sensor assembly comprising a coupling element 210. In alternative embodiments, the coupling element 210 is provided in a base plate, such as the base plate as illustrated in FIG. 1. Thus, the discussion below relating to the coupling of the monitor device 6 to the coupling element 210 is likewise applicable to the situation where the coupling element 210 and associated electrodes and terminals (sensing means) are provided in a base plate.

The monitor device 6 comprises a monitor device housing 100. The monitor device 6 comprises an interface opening 424, e.g. in a first rim part of the monitor device 6. The interface opening 424 is configured to receive the coupling element 210, such that the coupling element of the sensor assembly may be received by an appliance interface of the monitor device 6 through the interface opening.

The monitor device 6 is configured to engage with the coupling element 210 by a linear motion in the engagement direction 412 of the monitor device 6. The monitor device 6 is configured to disengage with the coupling element 210 by a linear motion in the disengagement direction 413 of the monitor device 6. As seen, the engagement direction 412 and the disengagement direction 413 may be opposite.

The plurality of terminals 212 of the sensor patch 50 is provided on the coupling element 210. The plurality of terminals of the monitor device 6 may be provided inside the opening 424, such as to connect to the plurality of terminals 212 of the sensor patch 50 when the monitor device 6 is coupled to the sensor patch 50.

The monitor device 6 comprises a locking mechanism configured to lock the monitor device 6 in a coupled position with the sensor patch 50. The locking mechanism of the monitor device 6 is configured to cooperate with the coupling element 210 of the sensor patch, such as to cooperate with a hole 428 of the coupling element 210. The hole 428 in the illustrated example comprises a hole extending through the coupling element 210. The locking mechanism of the monitor device 6 may comprise a locking component, e.g. a pin, positioned inside the opening 424 and being configured to protrude through the hole 428.

The locking mechanism comprises a locking element 430, e.g. a first button or a latch as illustrated. The locking element 430 further comprises a locking element protrusion 431. The locking element 430 is deflectable in a first direction 432 and the locking element protrusion 431 is configured for the user to pull/push the locking element 430 in a second direction 433, e.g. opposite the first direction 432. The locking element 430 may be configured for a rotational movement, e.g. relative to the monitor device housing 100, about a locking element axis, e.g. substantially parallel to the first rim part and/or may be substantially parallel to the length and/or longitudinal axis of the monitor device. The locking element axis may be substantially perpendicular to the engagement direction 412 and the disengagement direction 413.

Hence, the user may linearly move the monitor device 6 in the engagement direction 412, such that the coupling element 210 is received in the opening 424, and hereafter, the user may push the locking element 430 in the first direction to lock the locking mechanism, and the monitor device is locked, such as retained, in the coupled position with the coupling element 210. Subsequently, in order to remove the monitor device 6, the user may push/pull the locking element protrusion 431 in the second direction 433 to unlock the locking mechanism, and the user may disengage the monitor device 6 from the coupling element 210 by moving the monitor device 6 in the disengagement direction 413.

The locking element 430 may be configured to be positioned in a plurality of predefined positions, e.g. including a locked position and a first unlocked position. The predefined positions may be positions of the locking element 430 where a greater force is needed to change the position of the locking element 430. The plurality of predefined positions may include a second unlocked position, such as a cleaning position, where the locking element 430 is opened to allow cleaning of the interior of the appliance interface. The locking element may be brought from the locked position to the first unlocked position by movement in the second direction 433, e.g. by an angular movement of the locking element 430 of between 10-75 degrees. The locking element may be brought from the first unlocked position to the second unlocked position by (further) movement in the second direction 433, e.g. by an angular movement of the locking element 430 of between 90-170 degrees. The locking element 430 may be brought from the second unlocked position to the first unlocked position by movement in the first direction 432, e.g. by an angular movement of the locking element 430 of between 90-170 degrees. The locking element 430 may be brought from the first unlocked position to the locked position by (further) movement in the first direction 432, e.g. by an angular movement of the locking element 430 of between 10-75 degrees. An angular distance between the locked position to the second unlocked position may be between 100-200 degrees.

As will be described in relation to FIG. 6, the locking element 430, such as the entire locking element or at least parts of the locking element, may be transparent. Thereby, visual access to the appliance interface is provided, whereby the user can assess the functionality (such as the need for cleaning) of the interface.

Figure 5:
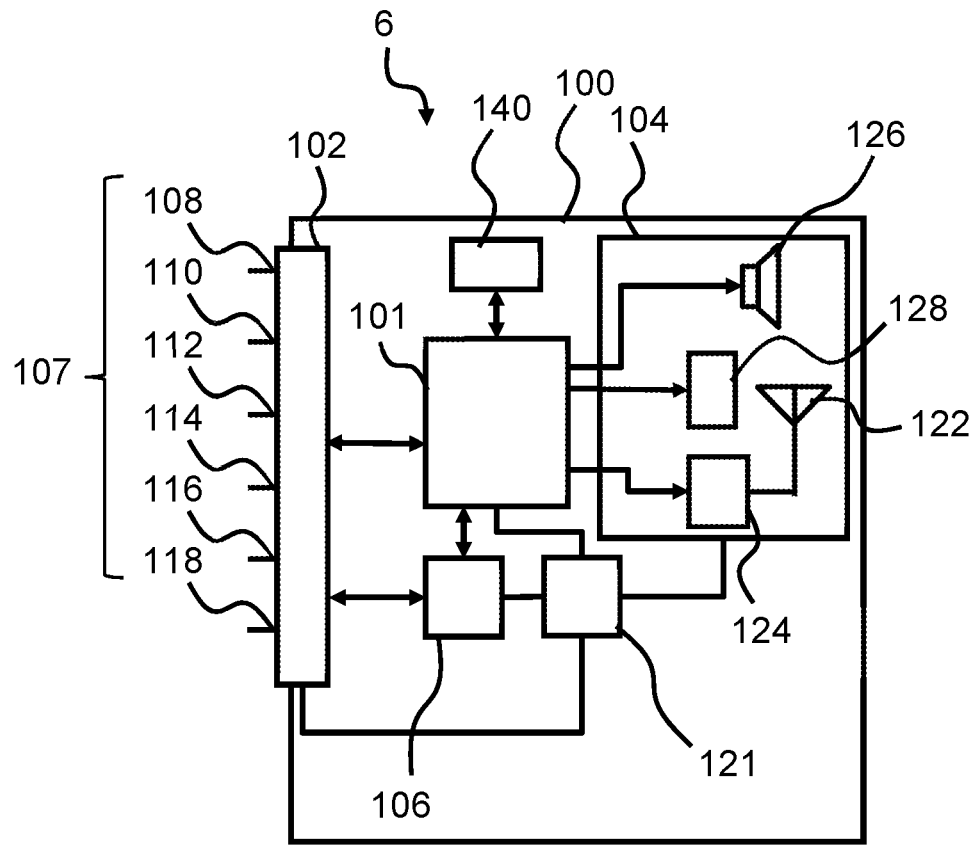
FIG. 5 is a schematic block diagram of an exemplary monitor device.

FIG. 5 is a schematic block diagram of an exemplary monitor device 6, such as the monitor device 6 as exemplified in relation to other figures. The monitor device 6 comprises a monitor device housing 100. The monitor device 6 comprises electronic circuitry, including a processor 101 and one or more interfaces. The one or more interfaces includes an appliance interface 102 and an optional accessory interface 104. The monitor device 6 comprises memory 106 for storing ostomy data and/or parameter data based on the ostomy data. The memory 106 is connected to the processor 101 and/or the appliance interface 102.

The appliance interface 102 is configured for electrically and/or mechanically connecting the monitor device 6 to the ostomy appliance, such as to a sensor assembly of the ostomy appliance. The appliance interface 102 comprises a plurality of terminals 107 for forming electrical connections with respective terminals of the sensor assembly. The appliance interface 102 comprises a ground terminal 108, a first terminal 110, a second terminal 112 and a third terminal 114. The appliance interface 102 optionally comprises a fourth terminal 116 and a fifth terminal 118.

The monitor device 6 comprises a power unit 121 for powering the monitor device and active components thereof, i.e. the power unit 121 is connected to the processor 101, the appliance interface 102, the accessory interface 104, and memory 106. The power unit comprises a battery and charging circuitry. The charging circuitry is connected to the battery and terminals of the appliance interface 102 for charging the battery via terminals of the appliance interface.

The accessory interface 104 of monitor device is configured for connecting the monitor device 6 to one or more accessory devices such as a smart phone. The accessory interface 104 comprises an antenna 122 and a wireless transceiver 124 configured for wireless communication with accessory device(s). Optionally, the accessory interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

Figure 6:
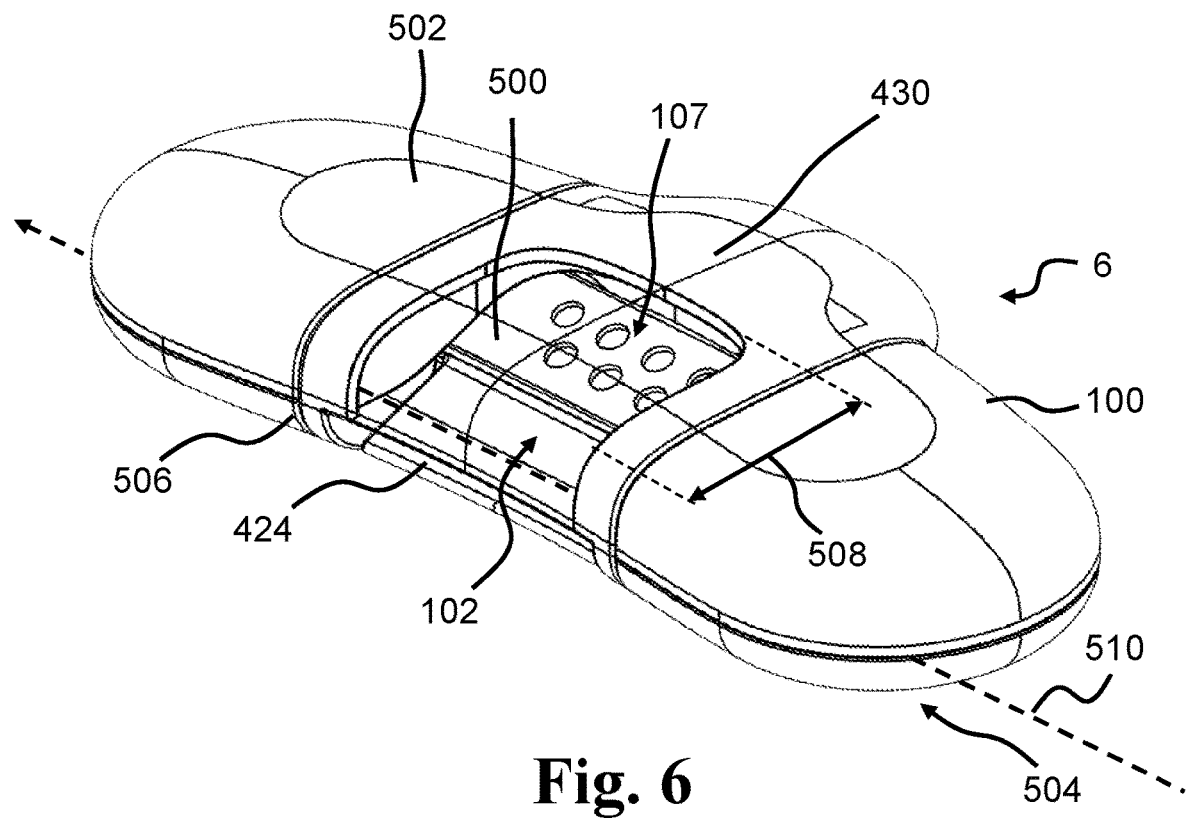
FIG. 6 schematically illustrates an exemplary monitor device.

FIG. 6 schematically illustrates an exemplary monitor device 6, such as the monitor device as described in relation to the previous figures. The monitor device 6 comprises a monitor device housing 100 and an appliance interface 102. The appliance interface 102 comprises a plurality of terminals 107. The monitor device 6 comprises an interface opening 424 for a coupling element of the sensor assembly to protrude through and into the appliance interface 102.

The monitor device has a first major side 502 and a second major side 504 opposite the first major side 502. The first major side 502 is configured to be facing away from the user when the monitor device 6 is coupled to the sensor assembly and the ostomy appliance is placed on the skin of the user. The interface opening 424 is provided in a first rim part 506 between the first major side 502 and the second major side 504.

The monitor device 6 comprises a transparent part 500 located near the interface opening 424. The transparent part 500 is positioned such that the plurality of terminals 107 of the appliance interface 102 is visible through the transparent part 500. Thereby allowing the user to see into the appliance interface 102 such as to understand its function as well as being able to see whether it needs to be cleaned. The transparent part 500 is provided on the first major side 502.

The transparent part may extend a first distance 508 in a direction substantially perpendicular to the first rim part 506. As illustrated, the first distance 508 may be more than 10%, such as more than 50% of a total distance between the first rim part 506 and an opposite second rim part.

The monitor device 6 comprises a locking mechanism configured to lock the coupling element of the sensor assembly in a received position of the appliance interface, and the monitor device 6 comprises a locking element 430 configured to lock and/or unlock the locking mechanism upon user interaction. As illustrated, in the presented example, the locking element 430 is configured to rotate relative to the monitor device housing 100 about a locking element axis 510 substantially parallel to the first rim part 506.

In the illustrated example, the transparent part 500 forms part of the locking element 430, i.e. the locking element 430 comprises the transparent part 500. In the illustrated example, the locking element 430 forms the interface opening 424. In the illustrated example, the transparent part 500 is forming a part of the perimeter of the interface opening 424. Hence, in the illustrated example the transparent part 500 is located at the interface opening 424 and extending from the interface opening 424 in a direction perpendicular to the first rim part 506.

Figure 7:
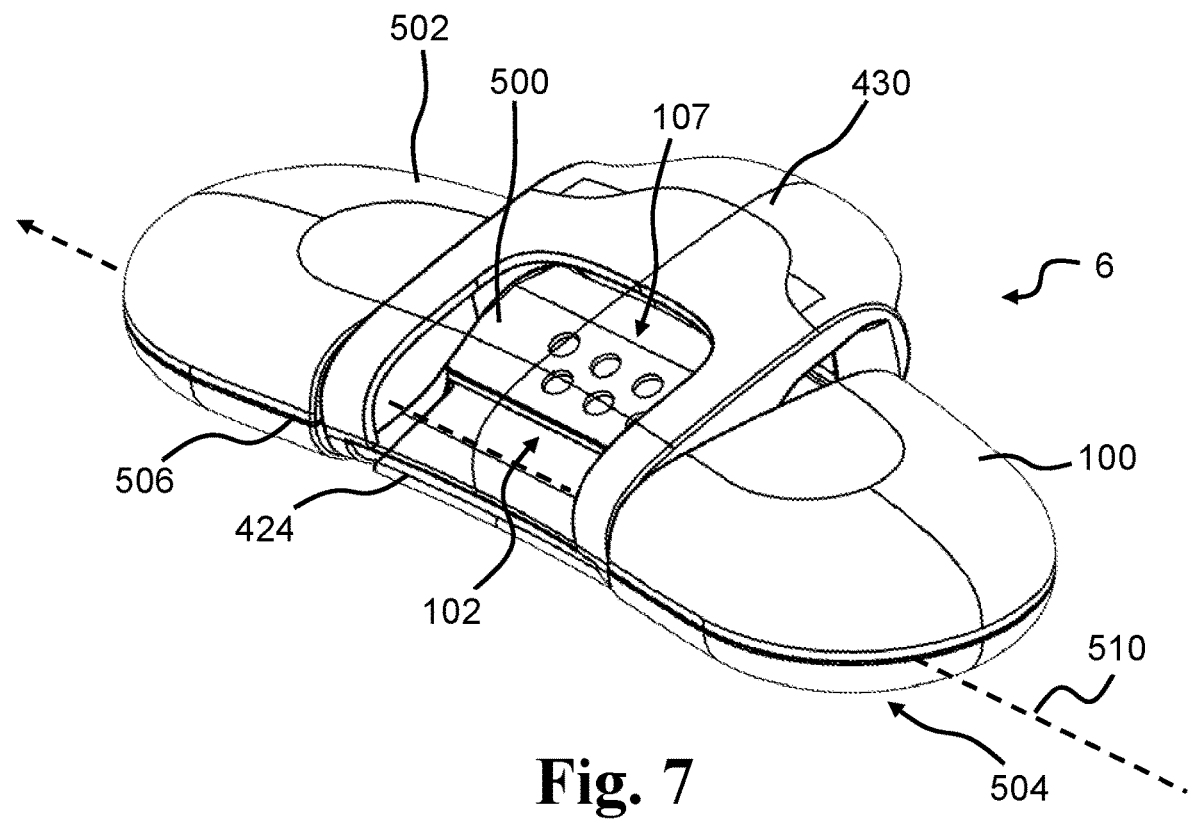
FIG. 7 schematically illustrates an exemplary monitor device.

FIG. 7 schematically illustrates the monitor device 6 as described with respect to FIG. 6. However, as illustrated in FIG. 7, the locking element 430 has been rotated relative to the monitor device housing 100 about the locking element axis 510 to be in a first unlocked position, as compared to the locked position as illustrated in FIG. 6.

Figure 8:
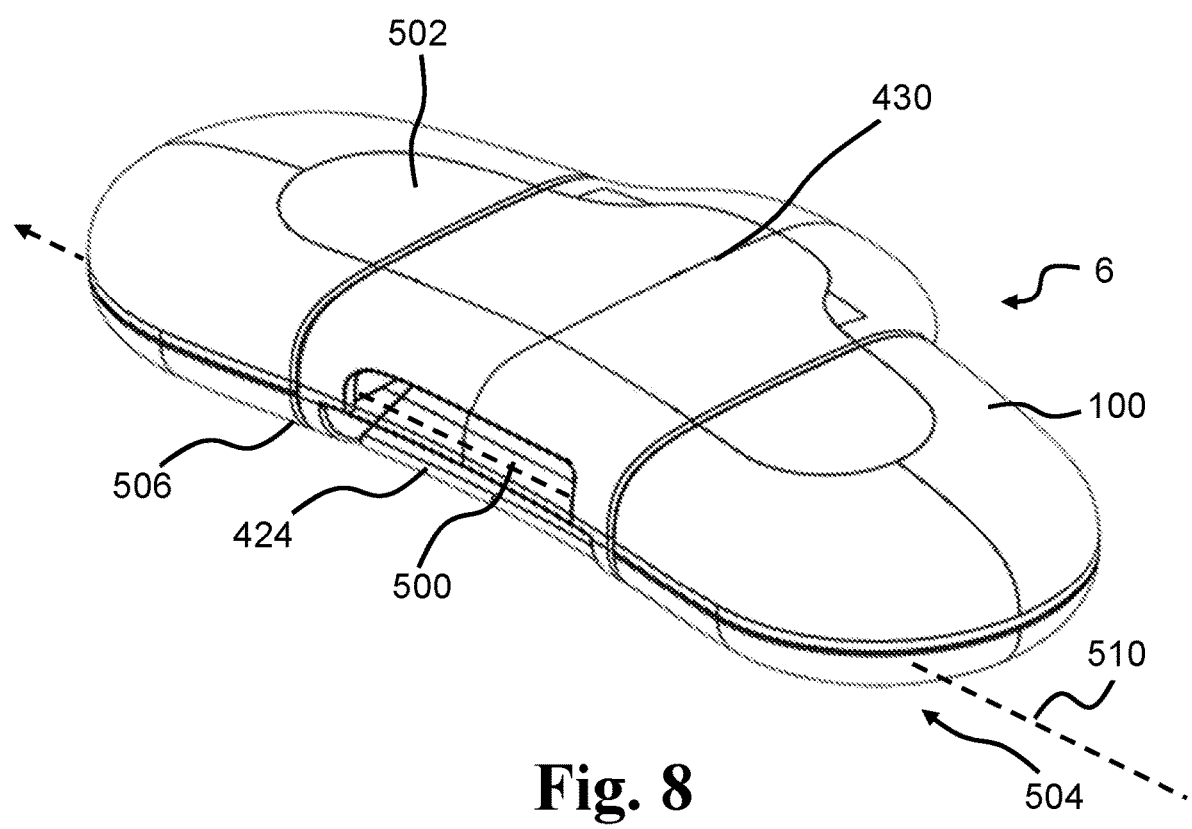
FIG. 8 schematically illustrates an exemplary monitor device.

FIG. 8 schematically illustrates an exemplary monitor device 6 similar to the monitor device as described with respect to FIGS. 6 and 7. However, transparent part 500 of the monitor device 6 is of a different size, i.e. smaller than the transparent part illustrated in FIGS. 6 and 7. A smaller transparent part may be easier to manufacture, while still providing some of the same benefits of the transparent part. For example, such smaller transparent part may still provide a visible clue to the user of where to insert the coupling element of the sensor patch or a base plate and may still provide some visibility of whether dirt has accumulated inside the appliance interface.

Figure 9:
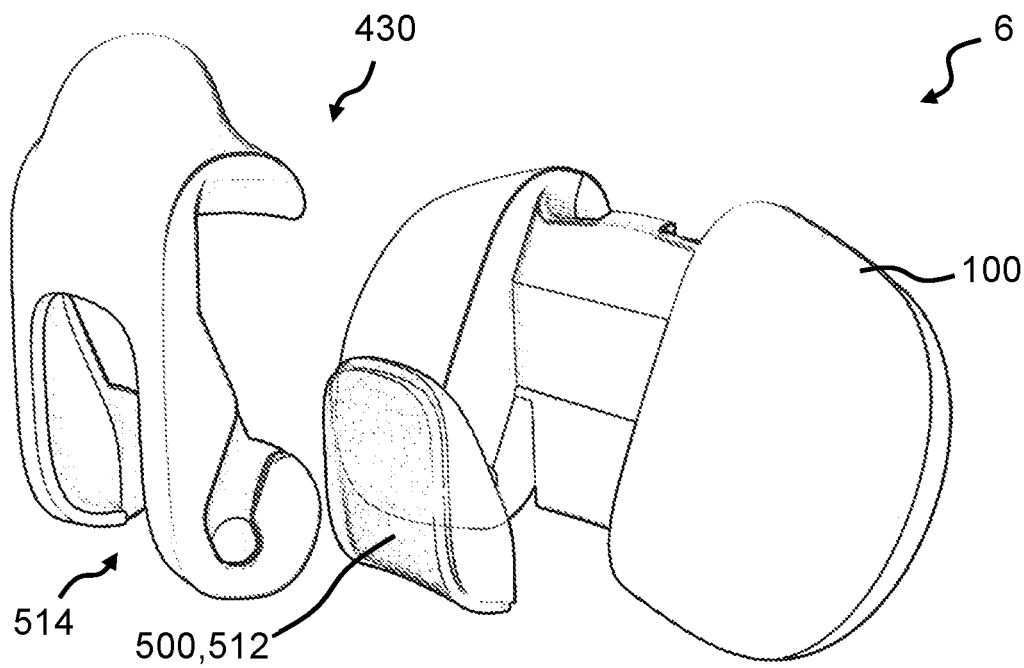
FIG. 9, schematically illustrates an exploded view of an exemplary monitor device, and FIG. 10, schematically illustrates an exploded view of an exemplary monitor device.
Figure 10:
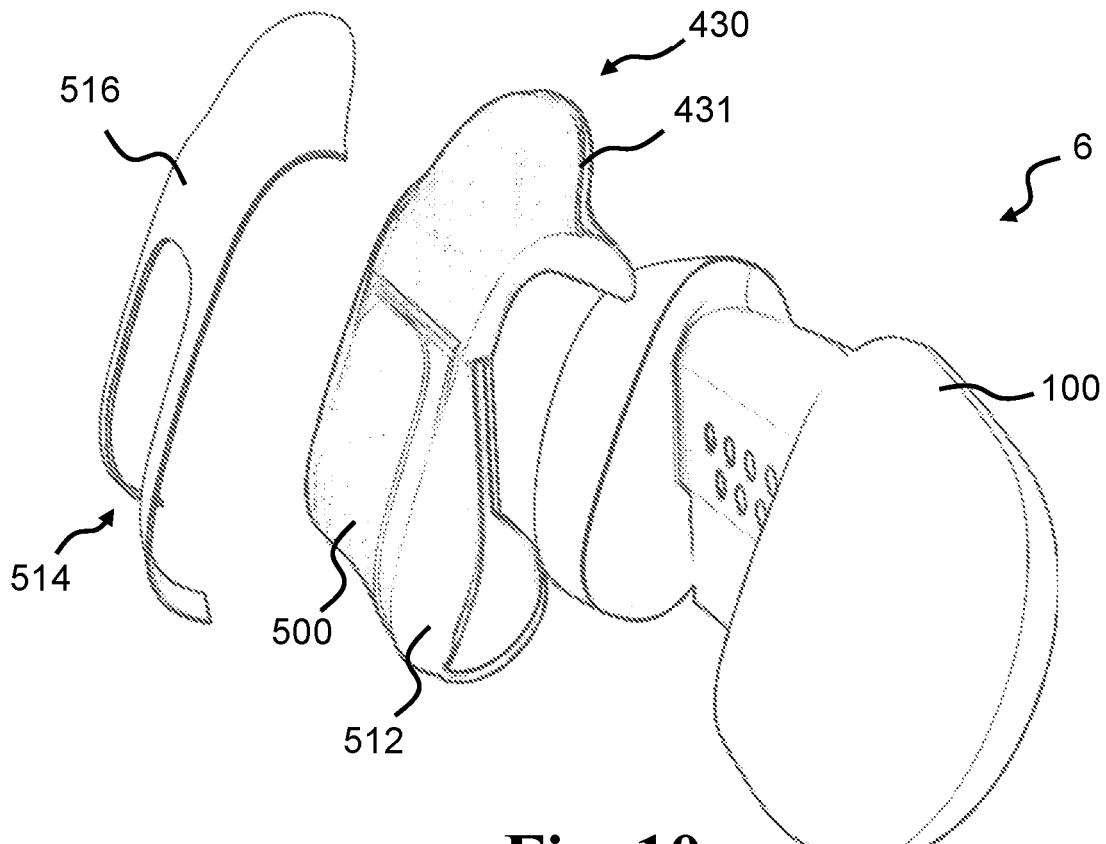

FIGS. 9 and 10, schematically illustrate exploded views of exemplary monitor devices 6, e.g. the exemplary monitor device 6 as illustrated in relation to FIGS. 6 and 7.

As seen in FIG. 9, the transparent part 500 may be provided by a transparent member 512, which is configured to fill an opening 514 of the locking element 430. Alternatively, as illustrated in FIG. 10, the transparent part 500 may be provided by a transparent member 512, which is configured to extend throughout the extension of the locking element 430, and the locking element 430 comprises a cover element 516 forming the opening 514 to define the transparent part 500.

The exemplary monitor device 6 as illustrated in FIG. 10 further have the advantage that the transparent member 512, which may be coloured differently than the remainder of the monitor device 6 (the transparent member may be coloured as described with respect to the transparent part above), may also form a locking element protrusion 431 configured for the user to pull/push the locking element 430 to unlock the locking mechanism. Thereby, the transparent member 512 may be visible at the position for the user to interact with to unlock the locking mechanism, providing the user with an indication of where to pull/push to unlock the device.

Furthermore, another advantage of the exemplary monitor device 6 as illustrated in FIG. 10 is that the sides of the transparent member 512 may be visible in unlocked position(s) of the locking element, indicating to the user that the locking member is not in the locked position and needs to be engaged in order to lock the locking mechanism properly.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A monitor device for coupling to a sensor assembly of an ostomy appliance, the monitor device comprising:
    a monitor device housing,
    electronic circuitry, and
    an appliance interface configured for coupling the monitor device to the sensor assembly, the appliance interface comprises a plurality of terminals for connecting with a plurality of electrodes of the sensor assembly, wherein a coupling element of the sensor assembly is receivable by the appliance interface through an interface opening,
    wherein the monitor device comprises a transparent part, and wherein the transparent part is located near the interface opening.

2. The monitor device according to claim 1, wherein the transparent part is positioned such that the plurality of terminals of the appliance interface is visible through the transparent part.

3. The monitor device according to claim 1, wherein the monitor device has a first major side and a second major side opposite the first major side, the first major side being configured to face away from a user when the monitor device is coupled to the sensor assembly and the ostomy appliance is placed on the skin of the user, wherein the interface opening is provided in a first rim part between the first major side and the second major side.

4. The monitor device according to claim 3, wherein the transparent part is provided on the first major side.

5. The monitor device according to claim 3, wherein the transparent part extends a first distance in a direction substantially perpendicular to the first rim part.

6. The monitor device according to claim 5, wherein the first distance is more than 10% of a total distance between the first rim part and an opposite second rim part between the first major side and the second major side.

7. The monitor device according to claim 5, wherein the first distance is more than 5 mm.

8. The monitor device according to claim 3 and further comprising a locking mechanism configured to lock the coupling element of the sensor assembly in a received position of the appliance interface, and the monitor device comprising a locking element configured to lock and/or unlock the locking mechanism upon user interaction with the locking element.

9. The monitor device according to claim 8, wherein the locking element is configured to rotate relative to the monitor device housing about a locking element axis substantially parallel to the first rim part.

10. The monitor device according to claim 8, wherein the locking element comprises the transparent part.

11. The monitor device according to claim 8, wherein the locking element forms the interface opening.

12. The monitor device according to claim 3, wherein the coupling element of the sensor assembly is configured to be received through the interface opening along an engagement direction, and wherein the engagement direction is substantially perpendicular to the first rim part.

13. The monitor device according to claim 1, wherein the transparent part is located less than 3 mm from the interface opening.

14. The monitor device according to claim 1, wherein the transparent part forms a portion of a perimeter of the interface opening.

15. The monitor device according to claim 1, wherein the transparent part at least partly allows transmittance of at least a subset of wavelengths of visible light.

16. The monitor device according to claim 15, wherein the transparent part allows transmission of more than 20% of at least a subset of wavelengths of visible light.

17. The monitor device according to claim 1, wherein the transparent part has a first colour, the monitor device housing has a second colour, and the second colour is different from the first colour with a colour distance of more than 10 as measured according to CIEDE2000 colour distance metric.

18. The monitor device according to claim 1, wherein the transparent part is located less than 2 mm from the interface opening.

19. The monitor device according to claim 1, wherein the transparent part is located less than 1 mm from the interface opening.

20. The monitor device according to claim 15, wherein the transparent part allows transmission of more than 60% of at least a subset of wavelengths of visible light.

* * * * *